United States Patent [19]

Christensen et al.

[11] 4,312,871
[45] * Jan. 26, 1982

[54] 6-, 1- AND 2-SUBSTITUTED-1-CARBADETHIAPEN-2-EM-3-CARBOXYLIC ACIDS

[75] Inventors: Burton G. Christensen, Scotch Plains; David H. Shih, Edison, both of N.J.

[73] Assignee: Merck & Co., Inc., Rahway, N.J.

[*] Notice: The portion of the term of this patent subsequent to Apr. 14, 1998, has been disclaimed.

[21] Appl. No.: 99,275

[22] Filed: Dec. 3, 1979

[51] Int. Cl.$^3$ .................... C07D 487/04; A61K 31/40
[52] U.S. Cl. ........................... 424/263; 260/245.2 T; 260/239 A; 424/269; 424/270; 424/274; 546/272; 542/401; 542/405; 542/413; 542/443
[58] Field of Search ................. 260/245.2 T; 424/274, 424/263, 269, 270; 546/272, 401, 405, 413, 443

[56] References Cited

U.S. PATENT DOCUMENTS 4,181,733  1/1980  Christensen et al. ........ 260/245.2 T
4,262,009  4/1981  Christensen et al. ........ 260/245.2 T
4,262,010  4/1981  Christensen et al. ........ 260/245.2 T
4,262,011  4/1981  Christensen et al. ........ 260/245.2 T Primary Examiner—Mary C. Lee
Attorney, Agent, or Firm—Frank M. Mahon; James A. Arno; Hesna J. Pfeiffer

[57] ABSTRACT

Disclosed are 6-, 1- and 2-substituted-1-carbadethiapen-2-em-3-carboxylic acids having the structure:

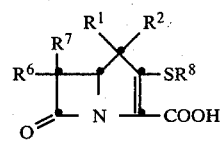

wherein: $R^1$, $R^2$, $R^6$, $R^7$ and $R^8$ are, inter alia, independently selected from the group consisting of hydrogen, alkyl, alkenyl, aryl and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

10 Claims, No Drawings

6-, 1- AND 2-SUBSTITUTED-1-CARBADETHIAPEN-2-EM-3-CARBOXYLIC ACIDS

BACKGROUND OF THE INVENTION

This invention relates to 6-, 1- and 2-substituted-1-carbadethiapen-2-em-3-carboxylic acids and derivatives thereof which are useful as antibiotics and which may be represented by the following generic structural formula (I):

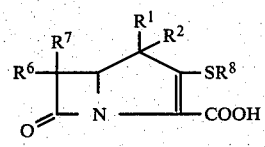

wherein $R^1$, $R^2$, $R^6$, $R^7$, and $R^8$ are independently selected from the group consisting of hydrogen, substituted and unsubstituted: alkyl, alkenyl, and alkynyl, having from 1–10 carbon atoms; cycloalkyl, spirocycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the alkyl has 1–6 carbon atoms; heteroaryl, heteroaralkyl, heterocyclyl and heterocyclylalkyl; wherein the substituent or substituents relative to the above-named radicals are selected from the group consisting of: amino, mono, di- and trialkylamino, hydroxyl, alkoxyl, mercapto, alkylthio, arylthio such as phenylthio, sulfamoyl, amidino, guanidino, nitro, chloro, bromo, fluoro, cyano and carboxy; and wherein the hetero atom or atoms in the above-named heterocyclic moieties are selected from the group consisting of 1–4 oxygen, nitrogen or sulphur atoms; and wherein the alkyl moieties of the above-recited substituents have 1–6 carbon atoms.

This invention also relates to the carboxyl derivatives of I which are antibiotics and which may be represented by the following generic structure (I):

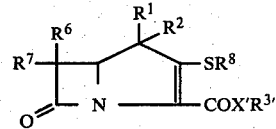

wherein X' is oxygen, sulphur or NR' (R'=H or lower alkyl having 1–6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^{3'}$ is given in greater detail below.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics; for unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an objection of the present invention to provide a novel class of antibiotics which are useful in animal and human therapy and in inanimate systems. These antibiotics are active against a broad range of pathogens which representaively include both gram positive bacteria such as *S. aureua, Strep. pyogenes,* and *B. subtilis,* and gram negative bacteria such as *E. coli,* Pseudomonas, *Proteus morganii,* Serratia, and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The process of the present invention may conveniently be summarized by the following reaction diagram:

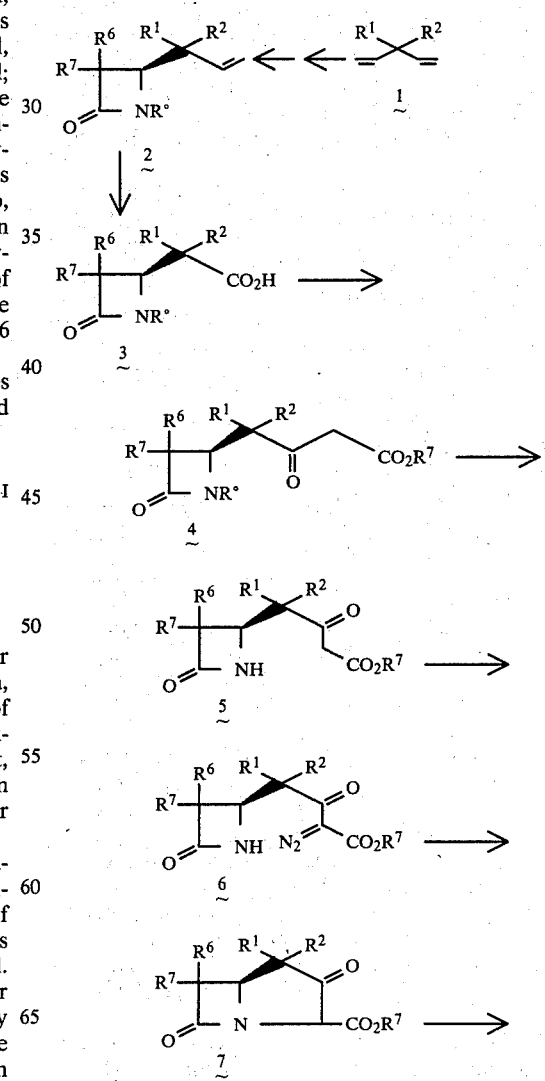

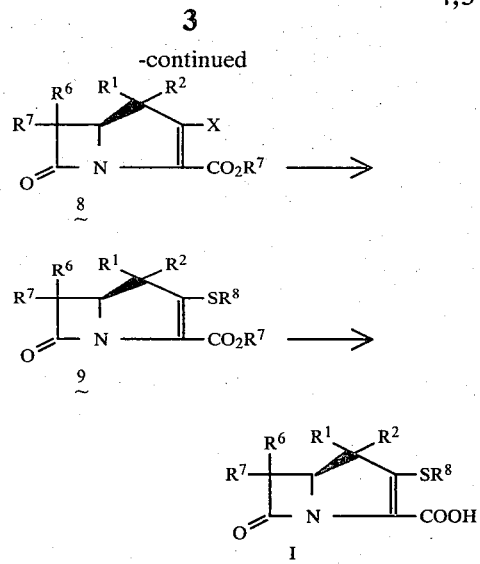

In words relative to diagram, the oxidation 2→3 is accomplished by treating 2 in a solvent such as methylenechloride, methanol, chloroform, or the like, with an oxidizing agent such as ozone, or the like, at a temperature of from −100° to 0° C. for from 0.1 to 4 hours, followed by treating the crude product with an oxidizing agent such as m-chloroperoxybenzoic acid, hydrogen peroxide, peracetic acid, or the like, at a temperature of from 0° C. to 100° C. for from 1 to 100 hours. R° is a readily removable protecting group and is defined below.

The addition 3→4 is accomplished by treating 3 with 1,1′-carbonyldiimidazole, or the like, in a solvent such as tetrahydrofuran, dimethoxyethane, or the like, at a temperature of from 0° to 50° C., followed by the addition of 1.1 to 3.0 equivalent of $(R^7O_2CCH_2CO_2)_2Mg$, at a temperature of from 0° to 50° C. for from 1 to 48 hours. $R^7$ is a pharmaceutically acceptable ester moiety or a readily removable carboxyl protecting groups such as p-nitrobenzyl, benzyl, or the like.

Removal of protecting group R°(4→5) is accomplished by acidic aqueous hydrolysis of 4 in a solvent such as methanol, ethanol, tetrahydrofuran, dioxane, or the like, in the presence of an acid such as hydrochloric, sulfuric, acetic or the like at a temperature of from 0° to 100° C. for from 2 to 18 hours.

The diazo species 6 is prepared from 5 by treating 5 in a solvent such as $CH_3CN$, $CH_2Cl_2$, THF, or the like, with an azide such as p-carboxybenzenesulfonylazide, toluenesulfonylazide, methanesulfonylazide, or the like, in the presence of a base such as triethylamine, pyridine, $(C_2H_5)_2NH$, or the like, for from 1 to 50 hours at 0°–25° C.

Cyclization (6→7) is accomplished by treating 6 in a solvent such as benzene, toluene, THF, or the like, at a temperature of from 50°–110° C. for from 1–5 hours in the presence of a catalyst such as bis (acetylacetonato)-Cu(II) [Cu(acac)$_2$], CuSO$_4$, Cu powder, Rh(OAc)$_2$ or Pd(OAC)$_2$. Alternatively, the cyclization may be accomplished by irradiating 6 through a pyrex filter (a wave length greater than 300 nm) in a solvent such as benzene, CCl$_4$, diethylether, or the like, at a temperature of from 0°–25° C. for from 0.5 to 2 hours. ["OAc"=acetate]

Establishment of leaving group X (7→8) is accomplished by acylating the keto ester 7 with an acylating agent RX such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, or the like, wherein X is the corresponding leaving group such as toluene sulfonyloxy, p-nitrophenylsulfonyloxy, methanesulfonyloxy, p-bromophenylsulfonyloxy and other leaving groups which are established by conventional procedures and which are well known in the art. Typically, the above acylation to establish leaving groups X is conducted in a solvent such as methylene chloride, acetonitrile or dimethylformamide, in the presence of a base such as diisopropylethylamine, triethylamine, 4-dimethylamino-pyridine or the like at a temperature of from −20° to 40° C. for from 0.5 to 5 hours. The leaving group X of intermediate 8 can also be halogen. The halogen leaving group is established by treating 7 with a halogenating agent such as $\phi_3PCl_2$, $\phi_3PBr_2$, $(\phi O)_3PBr_2$, oxalyl chloride or the like in a solvent such as $CH_2Cl_2$, $CH_3CN$, THF, or the like in the presence of a base such as diisopropylethylamine, triethylamine, or 4-dimethylaminopyridine or the like. [$\phi$=phenyl.]

The reaction 8→9 is accomplished by treating 8 in a solvent such as dioxane, dimethylformamide, dimethylsulfoxide, acetonitrile, hexamethylphosphoramide, or the like in the presence of an approximately equivalent to excess of the mercaptan reagent $HSR^8$ wherein $R^8$ as defined above. A representative mercaptan reagent is $HSCH_2CH_2NHR^{8'}$ wherein $R^{8'}$ is hydrogen or a readily removable N-protecting group such as p-nitrobenzyloxycarbonyl, o-nitrobenzyloxy carbonal, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent, $HSCH_2CH_2NHR^{8'}$, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step 9→I is accomplished by conventional procedures such as hydrolysis or hydrogenation. Typically 9 in a solvent such as dioxane-water-ethanol, tetrahydrofuran-aqueous dipotassium hydrogen phosphate-isopropanol or the like is treated under a hydrogen pressure of from 1 to 4 atmospheres in the presence of a hydrogenation catalyst such as palladium on charcoal, palladium hydroxide, or the like at a temperature of from 0° to 50° C. for from 0.5 to 4 hours to provide I.

Preparation of Starting Material 1 and 2

With respect to starting reagent 1, its preparation is generally described in J. Amer. Chem. Soc., 74, 661 (1952) by E. B. Reid and T. E. Gompf, J. Org. Chem., 23, 1063 (1958) by R. Ciola and K. L. Burwell, Jr., and Belgium Patent 632,193 (1963) by R. Polster and E. Scharf. The following scheme summarizes the preparation of 1.

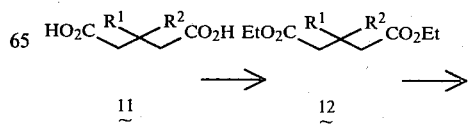

-continued

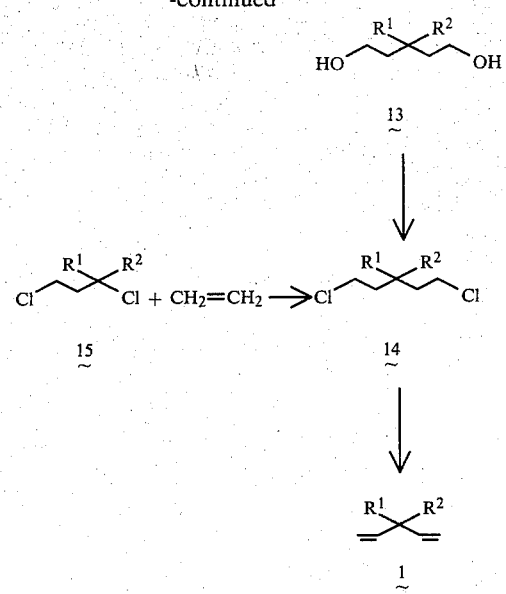

In words relative to the above scheme, the diester 12 is prepared by treating the diacid 11 with thionyl chloride at reflux for two hours followed by reacting with ethanol at 80° C. for 4 hours. Reduction of the diester 12 with lithium alumium hydride in ether at reflux for 4 hours followed by hydrolysis with 10% NaOH gives diol 13 which on further reaction with thionyl chloride gives dichloride 14. The dichloride 14 can be alternatively prepared by treating 15 with ethylene in the presence of alumium chloride. Treatment of the dichloride 14 with base such as 2-methylquinoline, DBU or sodium hydroxide in polyethylene glycol gives the expected 3-substituted 1,4-pentadiene 1.

Preparation of 2 is summarized in the following scheme:

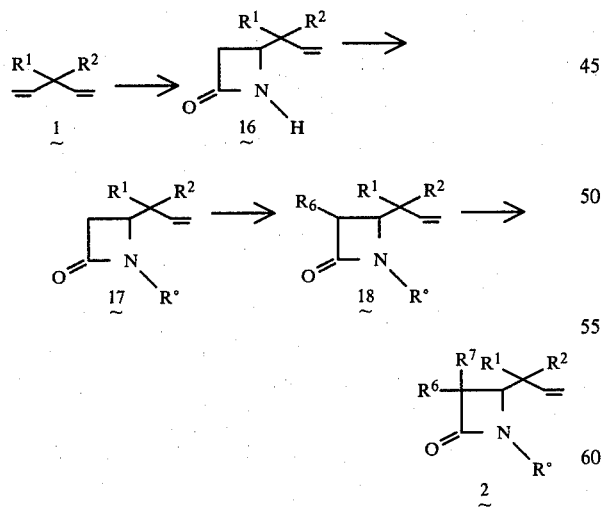

In words relative to above scheme, the substituted azetidinone 16 is prepared by reacting a 3-substituted 1,4-pentadiene 1 with chlorosulfonylisocyanate at 25° C. to 60° C. in a pressure bottle for 3–12 days, then the resulting mixture is hydrolyzed with aqueous sodium sulfite solution between pH 6.5–7.5 at 0° C. to 25° C. for from 5 min. to 60 min.

Azetidinone 16 is transformed (16→17) to establish the protecting group R° which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically R° is established by treating 1 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from −20° C. to 25° C. for from 0.5 to 24 hours in the presence of a base such as triethylamine, diisopropylethylamine, or imidazole.

Alkylation of 17 provides 18. Typically, 17 is treated with a strong base such as lithium diisopropylamide, sodium hydride, phenyl lithium or butyl lithium and the like in a solvent such as tetrahydrofuran (THF), ether, dimethoxyethane and the like at a temperature of from −80° C. to 0° C., whereupon the alkylating agent of choice, R X is added ($R^6$ is as described above and X is Iodo, chloro or bromo; alternatively the alkylating agent may be $R^6$-tosylate, $R^6$-mesylate or an aldehyde or ketone such as acetaldehyde and the like) to provide mono- alkylated species 18. When desired dialkylated species 2 may be obtained from 18 by repeating the alkylating procedure, 17→18.

In the foregoing description of the invention, suitable reagents $HSR^8$ (8→9) are representatively illustrated by the following list:

HSCH2CH2CH2NHCO2PNB,
PNBO2CNHCH2CH2CH2SX,

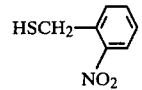

HSCH2CH2NHCO2PNB
HSC(CH3)2CH2NHCO2PNB,
HSφ,
HSCH2φ,
HSC(CH3)3,
HSCφ3,

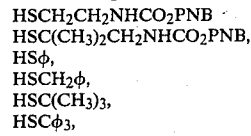

and the like (φ = phenyl; and PBN = p-nitrobenzyl),
CH3SH,
CH3CH2SH,
CH3(CH2)2SH,
(CH3)2CHSH,
CH3(CH2)3SH,
(CH3)2CH(CH2)2SH,
CH2=CHCH2SH,
CH≡CCH2SH,

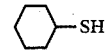

φ(CH2)3SH(φ = phenyl),
φ(CH2)2SH,
HO(CH2)2SH,
H2N(CH2)2SH,
H2N(CH2)3SH,
CH3(CH2)2NH(CH2)2SH,

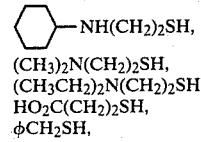

(CH3)2N(CH2)2SH,
(CH3CH2)2N(CH2)2SH,
HO2C(CH2)2SH,
φCH2SH,

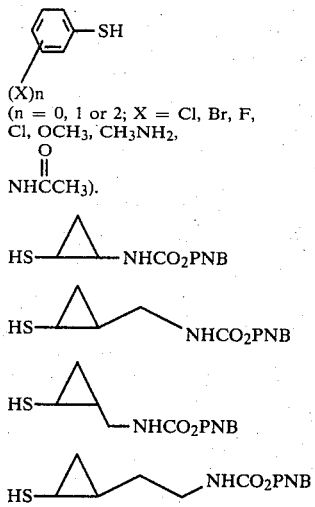

(X)n
(n = 0, 1 or 2; X = Cl, Br, F,
Cl, OCH₃, CH₃NH₂, $\overset{O}{\underset{\|}{NHCCH_3}}$).

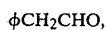

Similarly, suitable alkylating agents for establishing $R^6$ and/or $R^7$ at ultimate ring position 6 ($\underline{17} \rightarrow \underline{18} \rightarrow \underline{2}$) are:

φCH₂CHO,

φCH₂CH₂CHO,

CH₂O,

CH₃I,

φCH Br,

CH₃COCH₃.

Relative to the compounds of the present invention I:

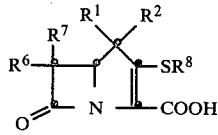

the most preferred values for $R^1$ and $R^2$ include:
ethyl,
propyl,
isopropyl,
cyclopropyl,
phenyl
benzyl
spiro-cyclopropyl The most preferred radicals for $R^6$ and $R^7$ are: $R^6 = H$ and $R^7$ is selected from hydroxymethyl, 1-hydroxyethyl, 1-hydroxypropyl, 2-hydroxypropyl, 2-hydroxyethyl; the most preferred values for $R^8$ are: aminoethylthio, aminopropylthio, aminocyclopropylthio, aminoisopropylthio, amidinoisopropylthio, and guanidinoethylthio.

The preferred esters used as protecting groups are those where $R^{3'}$ is benzyl, p-nitrobenzyl, o-nitrobenzyl, t-butyl, bromo-t-butyl, t-butyl-dimethylsilyl, trimethylsilyl, trichloroethyl; or $R^{3'}$ represents pharmaceutically acceptable ester moieties such as pivaloyloxymethyl, allyl, methallyl, (2-methylthio)-ethyl, 3-methyl-2-butenyl, p-t-butylbenzyl, 5-indanyl, 3-phthalidyl.

The compounds made available by the present invention are valuable antibiotics active against various gram-positive and gram-negative bacteria and, accordingly, find utility in human and veterinary medicine. Such sensitive bacteria representatively include: *Staphylococcus aureus, Escherichia coli, Klebsiella pneumoniae,* Serratia, *Salmonella typhosa,* Pseudomonas and *Bacterium proteus.* The resulting compounds may further be utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, or syrups; or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may taken such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and thorat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, or lotions.

Also, in addition to a carrier, the instant compositions may include other ingredients such as stabilizers, binders, antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases. The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

Especially preferred pharmaceutically acceptable salts and esters involving the carboxyl group of compounds of the present invention (I) are disclosed and claimed in co-pending U.S. patent application Ser. No. 861,314 (filed Dec. 16, 1977) now U.S. Pat. No. 4,181,733 issued Jan. 1, 1980 which application is directed, inter alia, to pharmaceutically acceptable salts and esters of the carboxyl group of thienamycin. It is precisely these salts and esters which are preferred in the present invention and they are prepared in a manner analogous to that disclosed in U.S. patent application Ser. No. 861,314, which is incorporated herein by reference. Thus, especially preferred salts include sodium, potassium, ammonium, and the like; and especially preferred esters include pivaloxymethyl, p-t-butylbenzyl, 5-indanyl, 3-phthalidyl, 3-methyl-2-butenyl, and the like. One should note that when, in the total synthesis outlined above, $R^{3'}$ is a pharmaceutically acceptable ester moiety, there is no need for the final deblocking step if it is desired to have the final product I in the form of a pharmaceutically acceptable ester.

Especially preferred embodiments of the present invention are those, as defined above, except that any unsubstituted amino group borne on radical $R^8$ of Structure I is derivatized according to the teachings of Belgium Pat. No. 848,545 (issued May 20, 1977); the resulting amino group being represented thusly (partial structure):

$$\sim\sim\sim N=C-X$$
$$\phantom{\sim\sim\sim N=C-}|$$
$$\phantom{\sim\sim\sim N=C-}Y$$

wherein X and Y are defined by the publication; species wherein X is H or lower alkyl and Y is $NH_2$ are especially preferred.

The following examples, illustrate but do not limit the product, process, compositional or method of treatment aspects of the present invention. All reaction temperatures are in °C.

EXAMPLE 1

Preparation of 3,3-Dimethyl-1,4-pentadiene

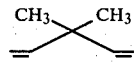

Procedure a

β,β-Dimethylglutaric acid (obtained from Aldrich Chemical Company) (one mole), is refluxed for 2 hours with thionyl chloride (68% excess). After removal of excess thionyl chloride, absolute ethanol (109% excess) is added slowly. The mixture is refluxed for 3 hours then distilled to collect the product, diethyl β,β-dimethylglutarate (98% yield).

To a suspension of lithium alumium hydride (24 g) in ether (860 ml) is added dropwise with rapid stirring a solution of diethyl β,β-dimethylglutarate (124 g in 250 ml ether). The mixture is refluxed for 6 hours, then cooled to room temperature. Water (25 ml) is added slowly. The mixture is then titrated with 10% NaOH until a clear organic layer is obtained. The organic layer is separated, dried over anhydrous sodium sulfate then evaporated in vacuo to give the resulting diol as an oil (90% yield), b.p. 95° at 1.0 mm. The 3,3-dimethyl-1.5-pentanediol (0.5 mole) is treated with thionyl chloride (1.05 mole) at reflux for 3 hours. After removal of excess thionyl chloride in vacuo, the 3,3-dimethyl-1,5-dichloropentane is obtained (90% yield).

3,3-Dimethyl-1.5-dichloropentane (41 g) is added dropwise at 170° C. to a mixture of 48 g of sodium hydroxide and 40 g of polyethylene glycol tetramer and the mixture is distilled to give 3,3-dimethyl-1,4-pentadiene (66%).

Procedure b

At −40° C., 1,3-dichloro-3-methylbutane (50 g) is mixed with aluminum chloride (5 g). The ethylene is bubbled through the mixture for 4 hours. The mixture is allowed to warm to room temperature and hydrolyzed with water. The mixture is extracted with ethyl acetate to give 3,3-dimethyl-1,5-dichloropentane.

A mixture of 0.5 mole of 3,3-dimethyl-1,5-dichloropentane, 2-methylquinoline (2 moles), and sodium iodide (0.1 mole) is refluxed in a flask equipped with a Vigreaux column at the top of which is a condenser and take-off. The diolefin 1 is collected during 8 hrs reaction. The product is dried over anhydrous sodium sulfate.

EXAMPLE 2

Preparation of 3-methyl-1,4-pentadiene

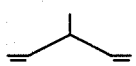

Following the procedure of Example 1(a), but replacing β,β-dimethylglutaric acid with an equivalent amount of β-methylglutaric acid, 3-methyl-1,4-pentadiene is obtained.

EXAMPLE 3

Preparation of
4-(1,1-dimethyl-pro-2-enyl)azetidin-2-one

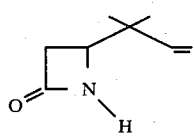

In a sealed tube, 3,3-dimethyl-1,4-pentadiene (9.6 g) and chlorosulfonyl isocyanate (14.2 g) are allowed to stand at room temperature for 6 days. The resulting mixture is diluted with methylene chloride and added slowly to a stirred aqueous solution which contains 20 g of $Na_2SO_3$ and 50 g of $K_2HPO_4$ at 0°–5° C. for 30 min. The organic layer is separated and dried over $Mg_2SO_4$. After evaporation, the crude product is chromatographed on silica gel GF eluting with EtOAc to give 3.

EXAMPLE 4

Preparation of 4-(1-methyl-pro-2-enyl)azetidin-2-one

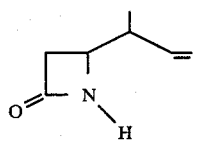

Following the procedure of Example 3, but replacing 3,3-dimethyl-1,4-pentadiene with 3-methyl-1,4-pentadiene, the title compound 4 is obtained.

EXAMPLE 5

Preparation of 5

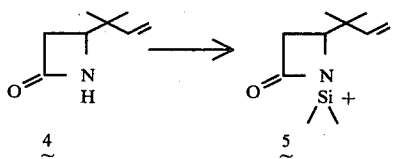

t-Butyldimethylchlorosilane (7.51 g) is added in one portion to an ice-cold, stirred, solution of 4-(1,1-dimethyl-prop-2-ene)-azetidin-2-one 6.54 g) and triethylamine (5.04 g) in anhydrous dimethylformamide (100 ml). The reaction mixture is stirred at 0°–5° C. for 1 hour and then allowed to warm to room temperature. Most of the solvent is removed under vacuum to give a residue which is partitioned between diethyl ether (250 ml) and water. The ethereal phase is washed with 2.5 N hydrochloric acid (50 ml), water (3×50 ml), and brine, dried with magnesium sulfate, filtered and evaporated under vacuum to provide a crude product which is purified by chromatography on silica gel (20% ether in petroleum ether) to yield 5.

EXAMPLE 6

Preparation of 6

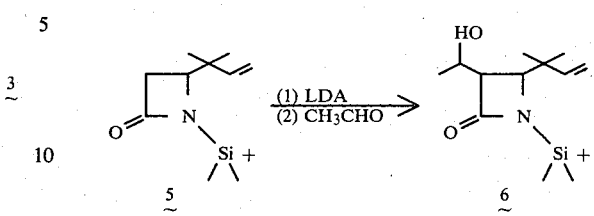

n-Butyllithium in hexane (26.25 mmol) is added slowly by syringe to a solution of diisopropylamine (26.25 mmol) in anhydrous tetrahydrofuran (100 ml) at −78° C. The resulting solution is stirred for 15 min. prior to the addition of a solution of 5 (25.0 mmol) in anhydrous tetrahydrofuran (25 ml). After stirring for 15 min. at −78° C., acetaldehyde (75 mmol) is added by syringe and the resulting solution is stirred at −78° C. for 5 min. Saturated aqueous ammonium chloride solution (15 ml) is added by syringe and the reaction mixture is allowed to warm to room temperature, then diluted with ether (250 ml) and washed with 2.5 N hydrochloric acid solution (2×50 ml), water (100 ml) and brine and dried over magnesium sulfate. Solvents are removed in vacuo and the residue is chromatographed on silica gel (1:1, ether: petroleum ether) to give the expected product 6.

EXAMPLE 7

Preparation of 7

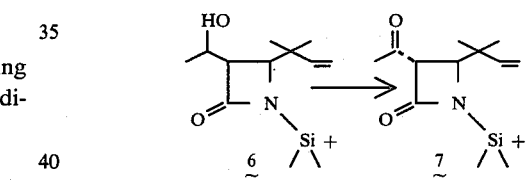

A. Trifluoroacetic anhydride (7.5 mmol) is added dropwise by syringe to a solution of dimethylsulfoxide (10 mmol) in anhydrous methylene chloride (15 ml) at −78° C. The resulting mixture is stirred at −78° C. for 20 min. A solution of 6 (5.0 mmol) in methylene chloride (15 ml) is added by syringe and the cooling bath is removed. After an additional 1 hr., the reaction mixture is diluted with methylene chloride (100 ml), washed with water (50 ml) and brine and dried over magnesium sulfate. Removal of solvents in vacuo yields crude product which is chromatographed on silica gel (2:1, petroleum ether: ether) to yield 7.

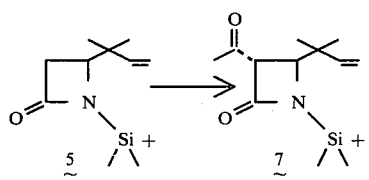

B. n-Butyllithium in hexane (4.10 mmol) is added by syringe to a solution of diisopropylamine (4.10 mmol) in anhydrous tetrahydrofuran (16 ml) at −78° C. The resulting solution is stirred at −78° C. for 15 min. prior to the addition of a solution of 1-(t-butyldimethylsilyl)-

4-(1,1-dimethyl-prop-2-enyl)-azetidin-2-one 5 (2.0 mmol) in anhydrous tetrahydrofuran (2 ml). After an additional 15 min. at −78° C., the reaction mixture is added via a Teflon tube to a mixture of N-acetylimidazole (4.1 mmol) in anhydrous tetrahydrofuran (16 ml) at −78° C. The resulting yellow reaction mixture is stirred at −78° C. for 15 min., then quenched by addition of saturated aqueous ammonium chloride solution (10 ml). The reaction mixture is diluted with ether (100 ml) and washed with 2.5 N hydrochloric acid solution (25 ml) water (25 ml) and brine. The organic phase is dried over magnesium sulfate and concentrated in vacuo to yield a crude product. This material is chromatographed on silica gel (2:1 petroleum ether: ether) to yield 7.

EXAMPLE 8

Preparation of 6

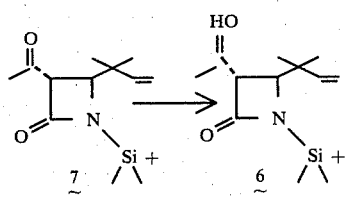

K-Selectride (potassium tri-(sec)-butylborohydride) in tetrahydrofuran (4.8 mmol) is added by syringe to a mixture of potassium iodide (2.0 mmol) and 7 (2.0 mmol) in anhydrous ether (20 ml) at room temperature. The resulting mixture is stirred at room temperature for 2.5 hours, then quenched by addition of glacial acetic acid (9.6 mmol). The resulting mixture is diluted with ethylacetate (100 ml) and filtered through celite. Removal of solvents in vacuo gives crude product which is chromatographed on silica gel (1:1 1 ether: petroleum ether) to yield 1.90 g (95%) of 6.

EXAMPLE 9

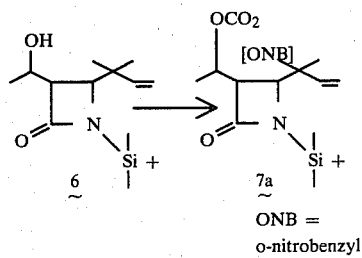

ONB = o-nitrobenzyl

Under anhydrous conditions at 0° C. a solution of 6 (3.50 g) in 60 ml methylene chloride is treated with 4-dimethylaminopyridine (3.32 g) and o-nitrobenzylchloroformate (5.88 g). The mixture is allowed to warm to room temperature and stirred for 1 hr. The resulting mixture is washed with 0.1 N HCl, water, brine and water. The organic layer is separated, dried over Na$_2$SO$_4$ and allowed to evaporate in vacuo to give crude products. The crude products, dissolved in 20 ml ether and chilled at −5° C., give the o-nitrobenzyl alcohol (0.5 g) which is separated by filtration. Purification by HPLC (silica gel) eluting with 40% ethylacetate/cyclohexane to gives 7a.

EXAMPLE 10

Preparation of 8

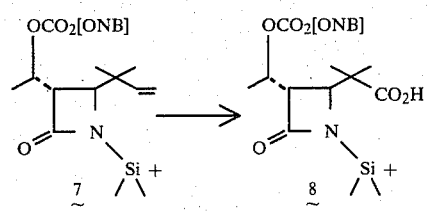

A solution of 7 (3.0 mmol) in dry methylene chloride (30 ml) is cooled to −78° C. (dry ice-acetone) and a stream of ozone is bubbled through until the reaction mixture becomes blue. The ozone flow is then stopped and the reaction is purged by bubbling through nitrogen until the blue color disappears. Solid m-chloroperbenzoic acid (3.0 mmol) is added and the cold bath is removed. When the reaction mixture reaches room temperature, the flask is fitted with a reflux condenser and the mixture is heated at reflux for three days. Removal of solvents in vacuo gives crude product which is chromatographed on silica gel (2% glacial acetic acid in methylene chloride) to 8.

EXAMPLE 10a

Preparation of 8a

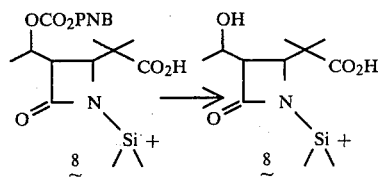

The acid 8 (1.0 mmol) is hydrogenated in 30 ml ethyl acetate under 1 atm H$_2$ in the presence of 0.1 mmol of 10% Pd/C at room temperature for 30 min. The mixture is filtered from catalyst. The filtrate is evaporated in vacuo to give 8a.

EXAMPLE 11

Preparation of 9

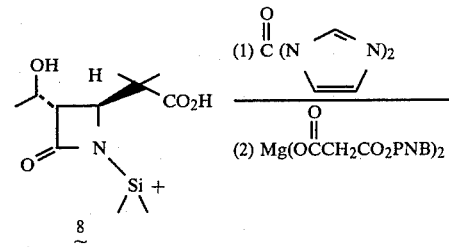

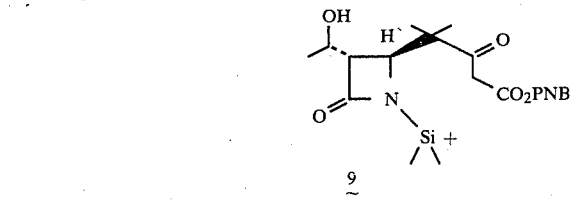

1,1'-Carbonylidiimidazole (1.10 mmol) is added in one portion to a solution of 8 (1.0 mmol) in anhydrous tetrahydrofuran (5 ml) at room temperature. The resulting solution is stirred at room temperature for 6 hours. In a second flask, magnesium ethoxide (5 mmol) is added in one portion to a solution of the mono-p-nitrobenzyl ester of malonic acid (10 mmol) in anhydrous tetrahydrofuran (25 ml). The resulting mixture is stirred at room temperature for 1 hr., then the tetrahydrofuran is removed at the pump and the residue is triturated with ether to yield the magnesium salt. This magnesium salt is then added to the first reaction flask and the resulting mixture is stirred at room temperature for 18 hrs. The reaction mixture is then poured into 50 ml of ether, washed with 0.5 N hydrochloric acid solution (20 ml), water (20 ml), saturated aqueous sodium bicarbonate solution (20 ml), brine and dried over magnesium sulfate. Removal of solvents in vacuo gives crude product which is chromatographed on silica gel (ether) to yield 9.

EXAMPLE 12

Preparation of 10.

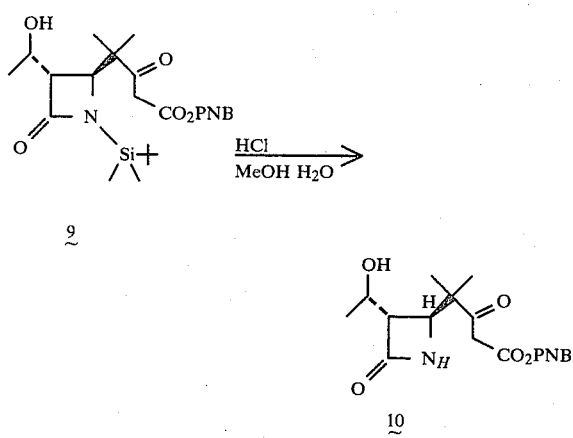

A solution of 9 (1.0 mmol) in 20 ml of 9:1 (v/v) methanol-water is cooled to 0° C. Concentrated hydrochloric acid (0.34 ml) is added and the resulting solution is stirred at 0° C. for 15 min., then allowed to warm to room temperature. After 2.5 hrs., at room temperature the reaction mixture is diluted with ethyl acetate (25 ml), washed with water (10 ml) and brine, dried over magnesium sulfate and concentrated in vacuo to yield 10.

EXAMPLE 13

Preparation of 11

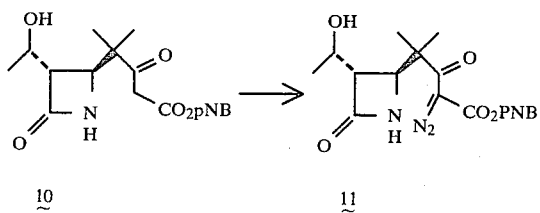

Triethylamine (263 mg) is added by syringe to a mixture of 10 (253 mg) and p-carboxybenzensulfonylazide (196 mg) in dry acetonitrile (6 ml) at 0° C. When addition is complete the cooling bath is removed and the reaction mixture is stirred at room temperature for 1 hour. The mixture is then diluted with ethyl acetate (50 ml) and filtered. The filtrate is concentrated in vacuo and the residue is chromatographed on a short silica gel column (ethyl acetate) to yield 11.

EXAMPLE 14

Preparation of 12

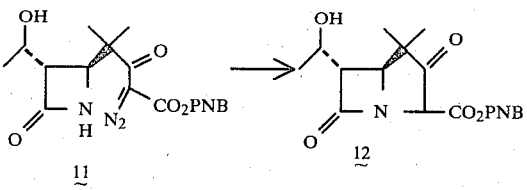

A suspension of 11 (56.4 mg) and rhodium (II) acetate (0.1 mg) in dry benzene (3 ml) is deoxygenated by bubbling through nitrogen for 10 minutes. The mixture is then heated to 78° C. for 1 hour. During heating the solid starting material gradually goes into solution. The mixture is then cooled, filtered to remove the catalyst, and the filtrate is concentrated in vacuo to yield 12.

EXAMPLE 15

Preparation of p-Nitrobenzyloxycarbonylaminoethanethiol

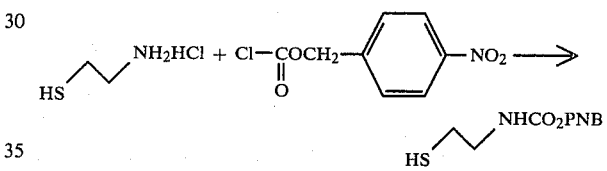

To 600 ml diethyl ether (Et$_2$O)-75 ml H$_2$O in an ice bath with stirring is added 3.2 g cysteamine hydrochloride (mw=114; 28.1 mmole). A solution of 7.14 g NaHCO$_3$ (mw=84; 85 mmole) in 75 ml H$_2$O is added. The ice bath is removed, and at room temperature a solution of 6.75 g p-nitrobenzylchloroformate (mw=216; 31.3 mmole) in 270 ml Et$_2$O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et$_2$O. The combined Et$_2$O layers are dried over anhydrous MgSO$_4$, filtered, and concentrated under a N$_2$ stream. The crystalline residue is slurried in a small amount of ether, filtered, and the pale yellow crystals are dried under high vacuum to give 4.7 g. p-nitrobenzyloxycarbonylaminoethanethiol (65% yield). NMR (CDCl$_3$):8.18 (d, J=8Hz, aromatic protons ortho to nitro), 7.47 (d, J=8Hz, aromatic protons meta to nitro), 5.27 (—NH—), 5.20 (s, —CH$_2$—NH—), 2.67 (m, —CH$_2$—SH), 1.35 (t, J=8.5 Hz, —SH) in ppm downfield from TMS. IR (CHCl$_3$) solution): carbonyl-1725 cm$^{-1}$. M.S.: molecular ion-256, (M-47) at 209, (M-136) at 120, +$CH_2\phi pNO_2$ at 136.

EXAMPLE 15a

Following the procedure of Example 15, N-p-nitrobenzyloxycarbonylaminocyclopropylthio is obtained when an equivalent amount of aminocyclopropylthio hydrochloride is substituted for the cysteamine hydrochloride of Example 15.

EXAMPLE 16

Preparation of 13

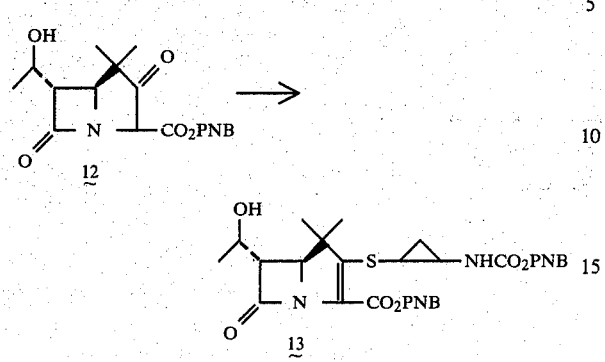

The starting material 12 (51 mg) is dissolved in acetonitrile (3 ml) and the resulting solution is cooled to 0° C. Diisopropylethylamine (22 mg) is added by syringe and the resulting solution is stirred at 0° C. for 1 minute prior to the addition of a solution of freshly recrystallized p-toluene sulfonic anhydride (51 mg) in dry acetonitrile (1 ml). The resulting solution is stirred at 0° C. for 1 hour to provide p-nitrobenzyl 4,4-dimethyl 3- (p-toluenesulfonyloxy)-6-[hydroxyethyl]-1-azabicyclo[3.2.0]hept-2-en-7-one-2-carboxylate, then cooled to −25° C. Diisopropylethylamine (80.5 mg) is added by syringe followed shortly thereafter by a solution of N-p-nitrobenzyloxycarbonylaminocyclopropylthiol (40 mg) in 1 ml of dry acetonitrile. The reaction mixture is then stored in a refrigerator for 70 hr. The mixture is diluted with 25 ml of ethyl acetate washed with brine and dried over magnesium sulfate. Solvents are removed in vacuo to yield crude product which is chromatographed on a silica gel plate to yield 13.

EXAMPLE 17

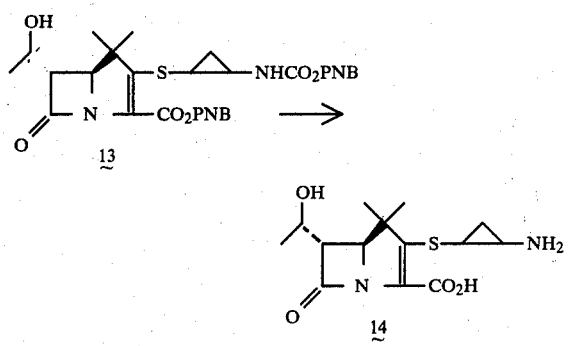

A mixture of 13 (10 mg) and 10% Pd/C-Bolhofer type in tetrahydrofuran (2 ml), 0.1 M dipotassium hydrogen phosphate solution (1.4 ml) and 2-propanol (0.2 ml) is hydrogenated at 40 psi on the Parr shaker for 30 minutes. The mixture is then filtered and the catalyst is washed with water. The combined filtrate and washings are extracted with ethyl acetate-ethyl ether then concentrated to ∼3 ml and lyophilized to give 14.

EXAMPLE 18

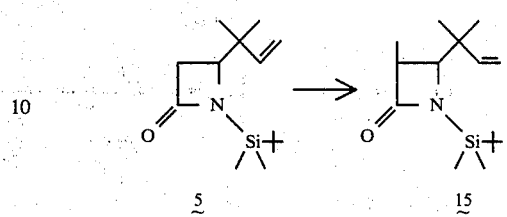

THF, 20 ml, is placed under $N_2$, treated with 1.54 ml diisopropylamine and cooled to −78° C. A solution of n-butyl lithium 1.97 M in hexane (5.6 ml) is added dropwise over 5 min. The reaction mixture is stirred at −78° C. for 10 min. and then treated with 5 (2.14 g) in 15 ml THF which is added dropwise over 5 min. After another 10 min. hexamethylphosphoramide (1.97 ml) is added. The mixture is stirred another 10 min., then treated with 2 ml of methyl iodide. The reaction mixture is stirred at −78° C. for 15 min. and allowed to warm to 25° C. and stirred for 15 min. The reaction mixture is diluted with EtOAc, washed once with pH 7 phosphate buffer then dried and evaporated. The residue is chromatographed on silica gel using 25% EtOAc/$C_6H_6$ as eluant to give 15.

EXAMPLE 19

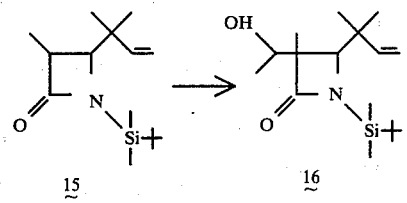

To a solution of 1.1 equivalents of freshly prepared lithium diisopropylamide in anhydrous tetrahydrofuran under a nitrogen atmosphere at −78° C. is added a solution of 15 in anhydrous tetrahydrofuran which has been cooled to −78° C. After two minutes, the resulting lithium enolate is treated with 3 equivalents of acetaldehyde. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 16.

EXAMPLE 20

Following the procedure of the foregoing Examples, the following substituted azetidinones useful in the preparation of the compound of the present invention are obtained when the suggested substitution of reagents is made.

|     | R¹ | R² | R⁶ | R⁷ |
|-----|-----|-----|-----|-----|
| (1.) | CH₃ | CH₃ | H | 2-NO₂-C₆H₄-CH₂OC(O)-OCH₂— |
| (2.) | CH₃ | Et | H | CH₃ |
| (3.) | CH₃ | cyclopropyl | H | C₆H₅C(O) |
| (4.) | CH₃ | C₆H₅CH₂ | H | CH₃C(O) |
| (5.) | CH₃ | CH(CH₃)₂ | H | C(CH₃)₂OH |
| (6.) | CH₃ | Ph | H | CH(CH₃)N₃ |
| (7.) | CH₃ | CH₃CH₂CH₂ | CH₃ | CH(CH₃)OCO₂CH₂-(2-NO₂-C₆H₄) |
| (8.) | Et | Et | CH₃CH₂ | CH₂CH₂OCO₂CH₂-(3-NO₂-C₆H₄) |
| (9.) | CH₃ | H | CH₃ | CH₃C(O) |
| (10.) | Et | CH₃ | H | CH(CH₃)OCO₂CH₂-(2-NO₂-C₆H₄) |
| (11.) | Et | Et | CH₃ | CH(CH₃)OCO₂CH₂-(2-NO₂-C₆H₄) |
| (12.) | cyclopropyl | CH₃ | CH₃ | CH₂CH₂OCO₂CH₂-(2-NO₂-C₆H₄) |
| (13.) | CH₃ | CH₃ | H | CH(CH₂OCH₂SCH₃)CH₂OCO₂CH₂-(2-NO₂-C₆H₄) |
| (14.) | CH₃ | Et | H | CH(CH₃)₂ |
| (15.) | H | cyclopropyl | H | CH(Ph)OCO₂CO₂CH₂-(2-NO₂-C₆H₄) |
| (16.) | CH(CH₃)₂ | CH₃ | H | Ph— |

-continued

| | R¹ | R² | R⁶ | R⁷ |
|---|---|---|---|---|
| (17.) | CH₃ | CH₃ | H | 3-pyridyl |
| (18.) | CH₃ | H | H | 4-pyridyl |
| (19.) | CH₃ | Et | H | CH(CH₃)SCO₂CH₂-(o-NO₂-C₆H₄) |
| (20.) | R¹ + R² = spirocyclopropyl | | H | CH(CH₃)OCO₂PNB |
| (21.) | CH₂CH₂Br | CH₃ | H | CH(CH₃)OCO₂PNB |

EXAMPLE 21

Following the foregoing text and Examples, the following species (I) are obtained when the β-lactams of Example 20 are carried through the standard procedure (Examples 10–14) to the corresponding bicyclic keto ester, followed by establishment of the thio side chain of choice and deblocking (Examples 16 and 17).

I

| Compound | R¹ | R² | R⁶ | R⁷ | R° | R⁸ |
|---|---|---|---|---|---|---|
| (1.) | CH₃ | —CH₃ | H | HOCH₂ | Na⁺ | cyclopropyl-NH₂ |
| (2.) | Et | —CH₃ | H | —CH₃ | Na⁺ | cyclobutyl-NH₂ |
| (3.) | CH₃CH₂CH₂ | —CH₃ | H | PhC(O)— | H | —(CH₂)₃N=CH-NH |
| (4.) | cyclopropyl | H | H | CH₃C(O)— | K⁺ | —C(CH₃)₂-NHC(=NH)-NH₂ |
| (5.) | cyclopropyl | —CH₃ | H | (CH₃)₂C(OH)— | CH₂OC(O)CCl₃ | —CH₃ |
| (6.) | PhCH₂ | CH₃ | H | CH₃CH(N₃)— | H | —C(CH₃)₂-NH₂ |
| (7.) | Ph | CH₃ | —CH₃ | CH₃CH(OH)— | H | cyclopropyl-NH₂ |
| (8.) | CH₃ | CH₃ | CH₃CH₂— | HOCH₂— | —CH₂-C₆H₄- | —C₂H₅ |
| (9.) | (CH₃)₂CH | CH₃ | CH₃ | CH₃C(O)— | H | —CF₂CH₂NH₂ |
| (10.) | C₄H₉ | —CH₂CH₂NH₂ | H | φCH₂CH(OH)— | H | —Ph |

-continued $$\begin{array}{c} R^2 \quad R^1 \\ R^6 \diagdown \mid \diagup \\ R^7 - \diagdown - SR^8 \\ \mid \quad \mid \\ O = \diagdown N \diagdown = CO_2R^\circ \end{array} \quad I$$

| Compound | $R^1$ | $R^2$ | $R^6$ | $R^7$ | $R^\circ$ | $R^8$ |
|---|---|---|---|---|---|---|
| (11.) | Et | $CH_3CH_2$ | $CH_3$ | $CH_3CH(OH)-$ | H | p-($CH_2NH_2$)phenyl |
| (12.) | $CH_3$ | cyclopropyl | $CH_3$ | $HOCH_2-$ | $Na^+$ | $CH_3$ |
| (13.) | cyclohexyl | $CH_3$ | H | $CH_3CH(OH)CH_2-$ | $(C_2H_5)_4N^+$ | $CH_2NH_2$ |
| (14.) | p-($CH_2NH_2$)phenyl | $CH_3$ | H | $CH_3CH(OCH_2SCH_3)-$ | H | $CH_2$-cyclopropyl-$NH_2$ |
| (15.) | Ph | $CH_3$ | H | Ph-CH(OH)- | H | $NH$-$CH_2CH_2C(=NH)-NH_2$ |
| (16.) | $CH_3$ | $CH_3CH(CH_3)-$ | H | phenyl | H | $CH(NH)(CO_2H)$-isopropyl |
| (17.) | $CH_3$ | $CH_3$ | H | pyridyl | $Na^+$ | $CH(NH_2)-$ |
| (18.) | Et | CH | H | methylpyridyl | H | pyrrolidinyl-O |
| (19.) | $CH_3$ | $CH_3$ | H | $CH_3CH(SH)-$ | $K^+$ | $-CH_3$ |
| (20.) | $R^1 + R^2 =$ spirocyclopropyl | | H | $CH_3CH(OH)-$ | Na | $-CH_2CH_2NHC(=NH)-H$ |

EXAMPLE 22

Preparation of Pharmaceutical Compositions

One such unit dosage form is prepared by mixing 120 mg of 1,1-dimethyl-6-(1-hydroxymethyl)-2-(2-aminocyclopropylthio)-1-carbadethiapen-2-em-3-carboxylic acid with 20 mg of lactose and 5 mg of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together larger capsules such as compressed tablets and pills can also be prepared. The following examples are illustrative of the preparation of pharmaceutical formulations:

| TABLET | PER TABLET |
|---|---|
| 1,1-dimethyl-6-(1-hydroxymethyl)-2-(2-aminocyclopropylthio)-1-carbadethiapen-2-em-3-carboxylic acid | 125 mg. |
| Dicalcium Phosphate | 192 mg. |
| Cornstarch, U.S.P. | 6 mg. |
| Lactose, U.S.P. | 190 mg. |
| Magnesium Stearate | Balance |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 1,1-dimethyl-6-(1-hydroxymethyl)-2-(2-aminocyclopropylthio)-1-carbadethiapen-2-em-3-carboxylic acid | 500 mg. |
| Diluent: Sterile Water for Injection | 5 cc. |
| OPTHALMIC SOLUTION | |
| 1,1-dimethyl-6-(1-hydroxymethyl)-2-(2-aminocyclopropylthio)-1-carbadethiapen-2-em-3-carboxylic acid | 100 mg. |
| Hydroxypropylmethyl cellulose | 5 mg. |
| Sterile Water to | 1 ml. |
| OTIC SOLUTION | |
| 1,1-dimethyl-6-(1-hydroxymethyl)-2-(2-aminocyclopropylthio)-1-carbadethiapen-2-em-3-carboxylic acid | 100 mg. |
| Benzalkonium chloride | 0.1 mg. |
| Sterile Water to | 1 ml. |
| TOPICAL OINTMENT | |
| 1,1-dimethyl-6-(1-hydroxymethyl)-2-(2-aminocyclopropylthio)-1-carbadethiapen-2-em-3-carboxylic acid | 100 mg. |
| Polyethylene Glycol 4000 U.S.P. | 400 mg. |
| Polyethylene Glycol 400 U.S.P. | 1.0 gram. |

What is claimed is:
1. A compound having the structure:

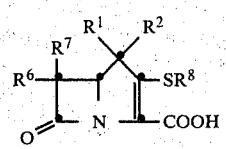

and the pharmaceutically acceptable salts thereof; wherein $R^1$, $R^2$, $R^6$, $R^7$ and $R^8$ are independently selected from the group consisting of hydrogen, ($R^1$ and $R^2$ are not hydrogen), substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; spirocycloalkyl having 3–6 carbon atoms; phenyl; aralkyl, aralkenyl, and aralkynyl wherein the aryl moiety is phenyl and the alkyl chain has 1–6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, iodo, cyano and carboxy; and wherein the alkyl moieties of the above-recited substituents have 1–6 carbon atoms; when $R^6/R^7$ is hydrogen and $R^7/R^6$ is 1-hydroxyethyl, then $R^8$ is not 2-aminoethyl or an N-derivative thereof.

2. A compound according to claim 1 wherein $R^1$ and $R^2$ are selected from alkyl, cycloalkyl, spirocycloalkyl, benzyl or phenyl; and $R^6$ is H or methyl and $R^7$ is alkyl, phenyl, aralkyl or hydroxyl-substituted alkyl, phenyl or aralkyl.

3. A compound according to claim 2 wherein $R^1$ and $R^2$ are selected from spirocyclopropyl, methyl, ethyl, isopropyl, t-butyl or phenyl and $R^7$ is 1-hydroxyethyl, methyl or hydroxymethyl.

4. A compound having the structure:

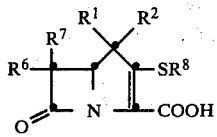

and the pharmaceutically acceptable salts thereof; wherein $R^1$, $R^2$, $R^6$, and $R^7$ are independently selected from the group consisting of hydrogen, ($R^1$ and $R^2$ are not hydrogen), substituted and unsubstituted: alkyl, alkenyl, and alkynyl, having from 1–10 carbon atoms; cycloalkyl, cycloalkyalkyl, and alkylcycloalkyl, having 3–6 carbon atoms in the cycloalkyl ring and 1–6 carbon atoms in the alkyl moieties; spirocycloalkyl having 3–6 carbon atoms; phenyl; aralkyl, aralkenyl, and aralkynyl wherein the aryl moiety is phenyl and the alkyl chain has 1–6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, iodo, cyano, and carboxy; and wherein the alkyl moieties of the above-recited substituents have 1–6 carbon atoms; when $R^6/R^7$ is hydrogen and $R^7/R^6$ is 1-hydroxyethyl, then $R^8$ is not 2-aminoethyl or an N-derivative thereof; $R^8$ is selected from the group consisting of:

H,
CH$_3$,
(CH$_2$)$_2$NH$_2$,
C(CH$_3$)$_2$CH$_2$NH$_2$,

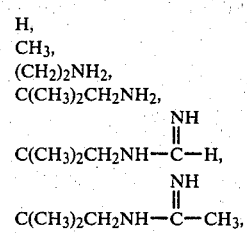

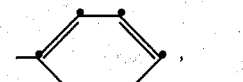

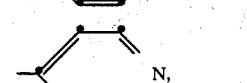

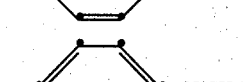

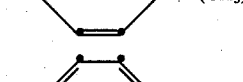

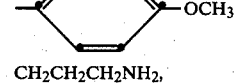

CH$_2$CH$_2$CH$_2$NH$_2$,
CH$_2$CH(CH$_3$)NH$_2$,

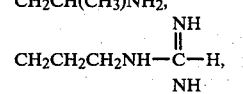

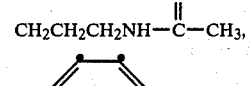

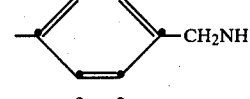

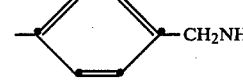

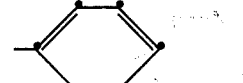

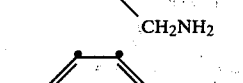

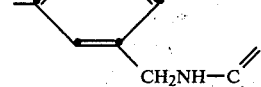

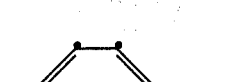

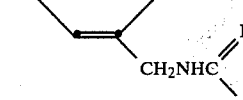

-continued

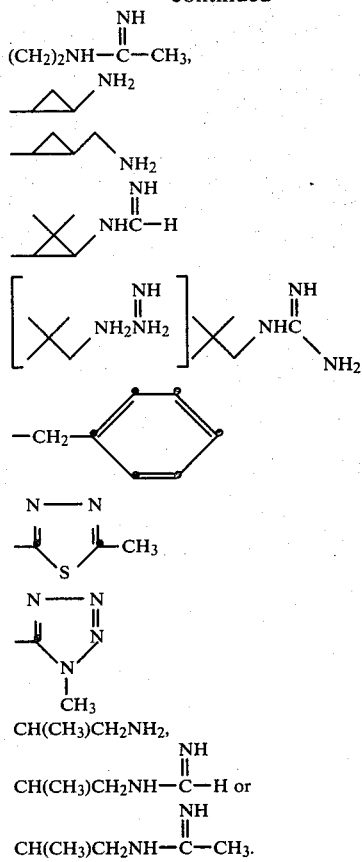

5. A compound according to claim 4 wherein $R^6$ is H or methyl; $R^7$ is selected from:

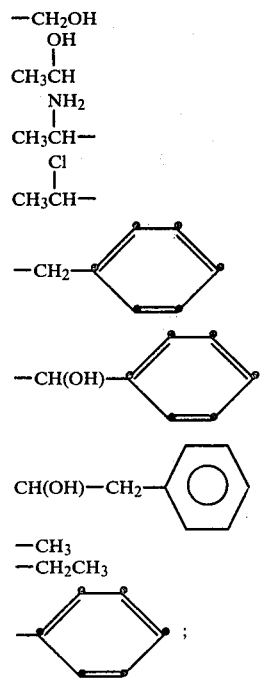

and $R^1$ and $R^2$ are selected from spirocyclopropyl; phenyl; cycloalkyl having 3–6 carbon atoms; alkyl having 1–6 carbon atoms; cyclopropylalkyl having 4–9 carbon atoms.

6. A compound according to claim 1 selected from the group consisting of:

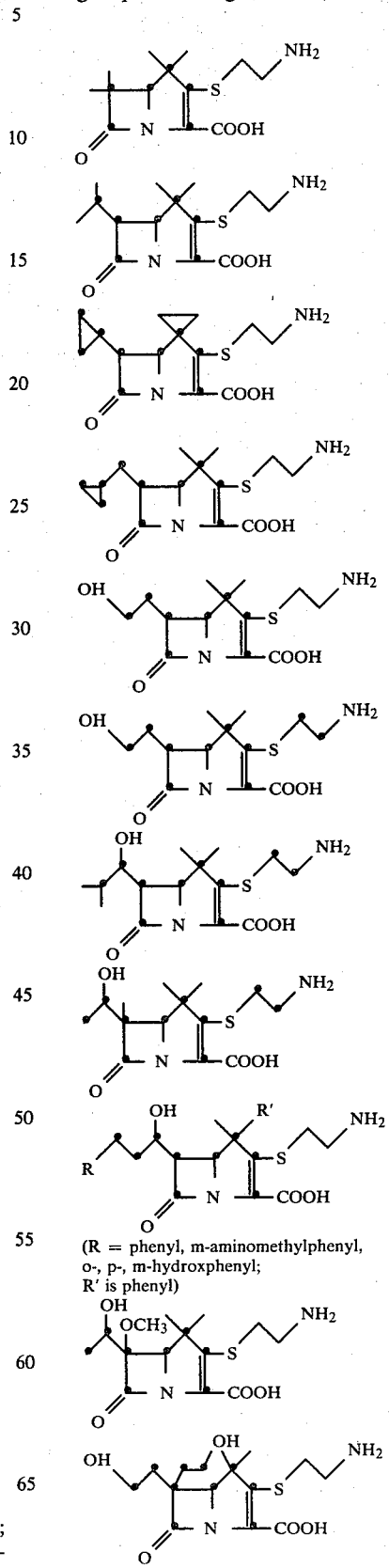

(R = phenyl, m-aminomethylphenyl, o-, p-, m-hydroxphenyl; R' is phenyl)

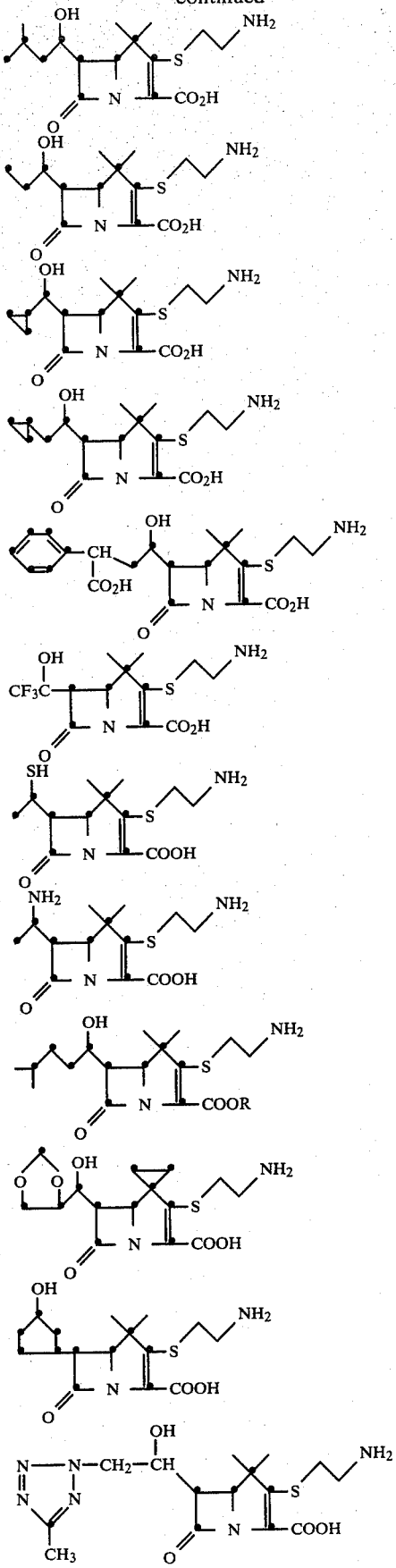

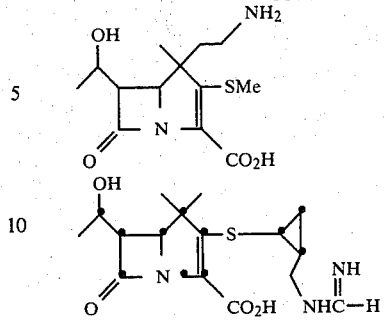

7. A compound according to claim 6 wherein the aminoethylthio side chain,

is replaced by a member of the group consisting of:

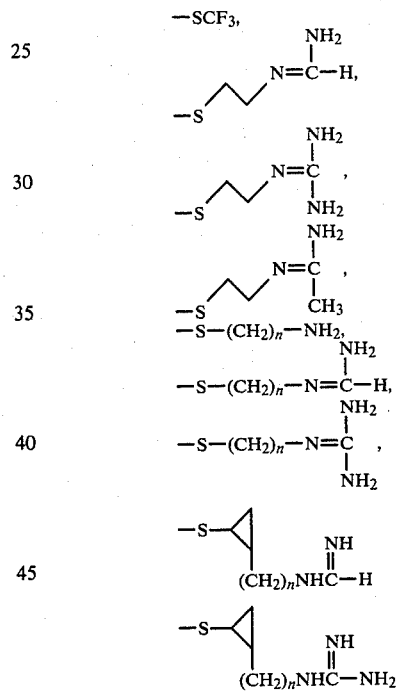

n=1, 3, 4, 5 or 6.

8. A compound having the structure:

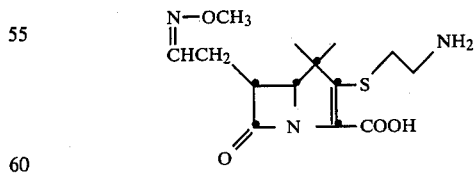

and the pharmaceutically acceptable salts thereof.

9. An antibiotic pharmaceutical composition comprising a therapeutically effective amount of a compound according to any one of claims 1–7 or 8 and a pharmaceutical carrier therefor.

10. A method of treatment comprising administering an antibiotically effective amount of the compound according to any one of claims 1–7 or 8.

* * * * *